United States Patent [19]

Wilson et al.

[11] 4,395,486

[45] Jul. 26, 1983

[54] METHOD FOR THE DIRECT ANALYSIS OF SICKLE CELL ANEMIA

[75] Inventors: Lois B. Wilson; John T. Wilson, both of Richmond County, Ga.; Robert F. Geever, Aiken County, S.C.

[73] Assignee: Medical College of Ga. Research Inst., Inc., Augusta, Ga.

[21] Appl. No.: 294,227

[22] Filed: Aug. 19, 1981

[51] Int. Cl.$^3$ .................... C12Q 1/68; G01N 33/50; C12P 19/34; C12N 15/00

[52] U.S. Cl. ........................................... 435/6; 435/7; 435/91; 435/172; 436/501; 436/504; 436/508

[58] Field of Search .................... 435/6, 7, 267, 270, 435/91, 172; 23/230 B; 424/1, 8, 12; 436/501, 504, 508, 801

[56] References Cited

U.S. PATENT DOCUMENTS 4,298,685 11/1981 Parikh et al. ........................... 435/7

OTHER PUBLICATIONS

Geever et al., PNAS, 78(8), 5081–5085 (Aug. 1981).
Kan et al., PNAS, 75(11), 5631–5635 (1978).
Nienhuis, New Eng. J. Med., 299(4), 195–196 (1978).
Wahl et al., PNAS, 76(8), 3683–3687 (1979).
Lawn et al., Cell, 21, 647–651 (1980).
Kan, Lancet, 2(8096), 910–912 (1978).
Phillips et al., PNAS, 75(5), 2853–2856 (1980).

*Primary Examiner*—Esther M. Kepplinger
*Attorney, Agent, or Firm*—Newton, Hopkins & Ormsby

[57] ABSTRACT

A direct diagnosis of sickle cell anemia by a restriction endonuclease assay with an enzyme which recognizes the nucleotide base sequence CTNAG (where N is any base), such as Dde I, for the sickle cell allele ($\beta^s$ gene) through molecular hybridization. Following enzyme cleavage, the resulting DNA restriction fragments are separated by molecular weight and transferred to filter paper. A probe is utilized for hybridization that is complementary to the 5' end of the $\beta$ globin gene. The banding pattern of individuals with normal hemoglobin shows two bands (approximately 175 bp and 201 bp), sickle cell trait individuals exhibit an additional band (approximately 376 bp) and individuals with sickle cell anemia show the band at approximately 376 bp with a concommitant loss of the band at approximately 175 bp. Prenatal and postnatal diagnosis of sickle cell anemia is possible with the present method.

27 Claims, 2 Drawing Figures

METHOD FOR THE DIRECT ANALYSIS OF SICKLE CELL ANEMIA

The Government has rights in this invention pursuant to Grant Number PCM 7909054 and Grant Number HL 23294 awarded by the National Science Foundation and the National Institute of Health, respectively.

BACKGROUND OF THE INVENTION (1) Field of the Invention

This invention relates to a diagnosis of sickle cell anemia and, more particularly, to a direct analysis of human hemoglobin genes by the use of restriction endonuclease Dde I and molecular hybridization procedures to detect sickle cell anemia.

(2) Description of the Prior Art

Sickle cell anemia is a debilitating genetic disorder that affects two of every thousand Blacks born in the United States. The disease is also prevalent in the Mediterranean area, as well as India. It is characterized by general weakness and pains in muscles and joints and can be fatal, frequently at an early age; victims do not live much beyond the age of 30. The disorder is caused by a single nucleotide base mutation in the globin gene which converts the glutamic acid codon (GAG) at amino acid position 6 to one for valine (GTG). That chemical abnormality produces red blood cells which are distorted into an inflexible sickle shape that can clog capillaries, blocking the flow of blood to the tissues.

The current test for sickle cell anemia diagnosis in fetuses is performed on samples of fetal blood obtained by fetoscopy. Through this procedure, a small sample of blood is taken from the fetus through the umbilical cord and then analyzed for sickle cells. The mutant protein migrates differently on the gel than the normal protein. While generally accurate, this diagnostic method is dangerous as it can cause a spontaneous abortion of the fetus 10 to 20% of the time.

Recombinant DNA techniques coupled with blot hybridization analysis have proven to be valuable tools for studying the molecular basis for hemoglobinopathies. Various researchers have used blot hybridization to confirm that $\delta\beta$-thalassemia and hereditary persistence of fetal hemoglobin are the results of gene deletions, whereas $\alpha$-thalassemia and $\beta$-thalassemia are due to both gene deletions and point mutations. One study has shown that at least one case of $\delta$-thalassemia is probably due to a base mutation.

These studies have also been extended to the clinical setting as methods for prenatal diagnosis of various genetic hematological conditions, generally the thalassemias. In addition, Kan and Dozy have reported, in Proc. Natl. Acad. Sci. USA 75, 5631–5635 (1978), the finding of a polymorphism for a Hpa I restriction endonuclease site in American Blacks 3' to the $\beta$ globin gene, which was shown to have a 60% association with the sickle cell allele. From their studies, they estimated that blot hybridization using this polymorphism alone could be successfully used for prenatal diagnosis of a sickle cell anemia in 36% of couples at risk. Phillips, et al. have combined the Hpa I analysis with a second polymorphism found in the $\gamma$ globin genes. In so doing, they have reported an extension of blot hybridization for prenatal diagnosis of sickle cell anemia to over 80% of the couples at risk. Proc. Natl'l. Acad. Sci. USA 77, 2853–2856 (1980). However, their analysis, which is safer than fetoscopies, requires family studies in order to establish the association of the polymorphic sites with the sickle cell allele. The analysis of polymorphisms requires analyzing DNA samples from both the mother and father to get 36% reliability and from both parents and one child already born to get 80% reliability. This limited application is a major disadvantage of these procedures.

A direct analysis of the sickle cell anemia should be possible by use of a restriction enzyme whose recognition sequence is created or eliminated by the sickle cell mutation. This approach would not require family studies, and should be useful for all couples at risk. Dr. A. Nienhuis has proposed such a direct analysis with restriction endonuclease Mnl I. N. Engl. J. Med. 299, 195–196 (1978). However, efforts in various laboratories have failed to attain the sensitivity requisite for the resolution by the DBM filter paper of the small [60–80 bp (base pairs)] fragments generated by this enzyme.

SUMMARY OF THE INVENTION

The disadvantages of the prior art methods are overcome by the present invention which utilizes a restriction enzyme which recognizes the nucleotide base sequence CTNAG (where "N" is any base), such as Dde I, for direct analysis of sickle cell anemia. Briefly, the analysis comprises the steps of either removing an effective amount of amniotic fluid and isolating DNA from the cells present in that fluid, or isolating DNA from peripheral blood lymphocytes, digesting the DNA with the restriction enzyme Dde I, separating the DNA fragments by molecular weight to form a band pattern and visualizing the band pattern or DNA fragments with a hybridization probe. The method may also include the step of transferring the DNA fragments to filter paper prior to hybridization. Normal individuals (AA) have approximately 175 bp and 201 bp blands on autoradiograms of the hybridized DNA segments, whereas sickle cell individuals (SS) have an approximate 376 bp band. Sickle cell trait individuals (AS) have the combination of approximate 175, 201 and 376 bp bands. Thus, the present invention can distinguish between AA, AS and SS individuals.

The procedure uses a restriction endonuclease, such as Dde I, which recognizes the base sequence CTNAG (wherein "N" is any base), for digestion of total genomic DNA. This restriction recognition site is present in normal DNA at codons 5 (CCT) and 6 (GAG), yet is not present in sickle cell DNA (CCT GTG) due to the sickle cell mutation. Following enzyme cleavage, the resulting restriction fragments are separated by molecular weight. One method of separating the fragments is by polyacrylamide gel electrophoresis and electrophoretically transferring the separated fragments to DBM paper. Another method is by high pressure liquid chromatography on reversed phase columns (RPC-5); the separated fragments are then immediately bound to filter paper (either DBM or nitrocellulose) for the sickle cell analysis.

For hybridization, applicants have isolated a probe which is complementary to the 5' end of the $\beta$ globin gene. This probe is nicktranslated to $1-2 \times 10^8$ dpm/$\mu$g of DNA, with hybridization occuring by the Southern blotting method. Southern, J. Mol. Biol. 98:503 (1975)

Besides radioactive labeling, probes for visualizing DNA fragments can be produced by using protein or biotin coupled nucleotides. Protein or biotin coupled nucleotides, once incorporated into the probe, can allow visualization of the $\beta$ globin gene fragments through the use of fluorescent antibodies binding to the protein or biotin molecules or to non-fluorescent antibodies also bound to such molecules. Such antibodies will bind specifically to DNA fragments to which hybridization has occurred since only hybridized fragments will have the initial protein or biotin nucleotide associated therewith. These complexes can then be visualized by illumination with ultraviolet light.

Applicants' current studies have been concerned with identification of the sickle cell allele ($\beta^s$ gene) within DNA isolated from peripheral DNA as well as amniotic fluid cell DNA for clinical antenatal diagnosis of sickle cell anemia.

BRIEF DESCRIPTION OF THE FIGURES OF DRAWING

DETAILED DESCRIPTION OF THE ILLUSTRATIVE EMBODIMENT

MATERIALS AND METHODS

Patients and blood collection

Figure 1:
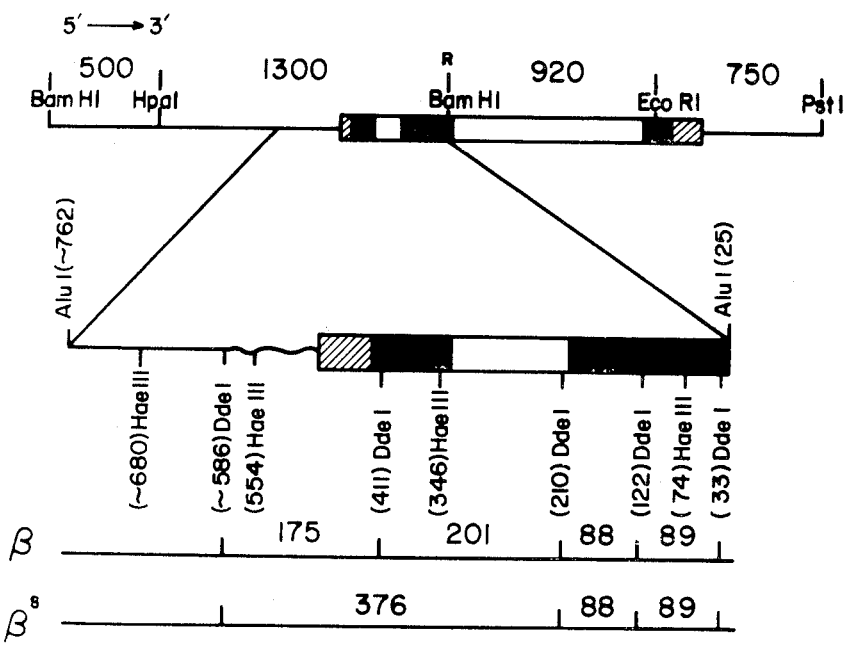
FIG. 1 is a restriction map of a portion of the human $\beta$ globin gene.

Patients with sickle cell anemia (SS), sickle cell trait (AS), and control individuals with no known hematological disorder (AA) were the subjects of the study. Approximately 10-20 ml of blood were collected in vacutainers with EDTA as anticoagulant. The samples were placed in ice and transported to the laboratory for immediate processing. Informed consent was obtained.

DNA Isolation

High molecular weight DNA was isolated from peripheral blood lymphocytes or cells present in the amniotic fluid by a method of that of Blin and Stafford. Nucl. Acid Res. 3, 2303-2308 (1976). Briefly, 10-20 ml samples were centrifuged at 3,000 rpm and the plasma or fluid fraction removed by aspiration. Residual amounts of plasma were extracted by repeated washes of the cell pellet with 0.9% NaCl. For DNA extractions from blood samples, the reticulocytes and older red cells were hemolyzed by the addition of two cell pellet volumes of sterile H$_2$O and the lymphocytes collected by centrifugation at 3,000 rpm for 15 min. The lymphocytes and amniotic fluid cells were lysed by the addition of 20 ml of lysing solution (0.05 M Tris pH 7.5, 0.5% SDS, 0.1 M NaCl, 0.001 M EDTA, 100 µg/ml proteinase k, Beckman) and incubated at 37° C. for 48 hrs. Following lysis, the solution was deproteinized by repeated chloroform-phenol (1:3) extractions and dialyzed overnight at 4° C. against 50 mM Tris pH 8, 10 mM EDTA, 10 mM NaCl. Nucleic acids were isolated by the addition of 2.5 volumes of ethanol followed by centrifugation at 9,000 rpm for 15 min. The pellet was resuspended in 10 mM Tris pH 7.5, 1 mM EDTA, incubated at 37° C. for 30 min with 50 µg/ml heat-treated RNAse (RNAse A, Sigma), and chloroform-phenol extracted. DNA was collected by ethanol precipitation followed by centrifugation as above, and redissolved in sterile H$_2$O at a concentration of about 0.2 mg/ml.

Separation of Fragment Lengths

A DNA fragment of approximately 1.8 kb was resolved by digestion of a recombinant DNA clone, which had a 4.4 kb DNA fragment of the $\beta$ globin gene integrated into the bacterial plasmid pBR 322; with Bam Hl and electrophoresis through 0.8% agarose in TEA buffer (40 mM Tris-HCl, pH 7.8, 20 mM NaAc, 2 mM EDTA). Recovery was attained by electroelution into dialysis tubing (Spectroapor 4) immersed in $\frac{1}{2}\times$TEA buffer, partial volume reduction by lyophilization, phenol-chloroform extraction and ethanol precipitation. Subsequent restriction enzyme digestions were performed with ten units enzyme per µg DNA (where 1 unit is that amount of enzyme which would digest µg of $\lambda$ DNA in one hour) and resolved on polyacrylamide gels containing 4% (w/v) acrylamide and 0.2% (w/v) N,N' methylenebisacrylamide. Fragments generated by Hae III digestion of $\phi\times$174 RF DNA were used as standards for approximate fragment length determinations.

DNA fragments resulting from restriction endonuclease DdeI digestion can also be separated by high pressure liquid chromatography on reversed phase columns (RPC-5) as set forth in Eshaghpour et al., 5 Nucleic Acids Res. 13-21 (1978). Through this procedure, DNA fragments can be separated and immediately bound to filter paper (either DBM or nitrocellulose) for the sickle cell analysis, thus eliminating the gel electrophoresis and DNA transfer steps. Such separation is also based on molecular weight.

Isolation and $^{32}$P-labeling of the Probe

Alu I digestion of pBR 322 $\beta$ Pst (4.4 kb) produces a 737 bp, 5' specific $\beta$ globin fragment. This fragment was resolved on and isolated from 4% polyacrylamide gels. On the average, 40% recovery was obtained following the electroelution process described above. Since preparations were contaminated with residual amounts of polyacrylamide, the quantity used as substrate for DNA Polymerase I (New England Biolabs, Inc.) was based on an estimate average recovery. Nick translations performed using $\alpha$-$^{32}$P-dCTP and $\alpha$-$^{32}$p-TTP (500µCi/mmol) purchased from New England Nuclear. Reaction conditions are those of Rigby et al., J. Mol. Biol. 113, 237-251 (1977), but with the buffer reported in Maniatis et al. Proc. Natl. Acad. Sci. USA 72, 1184-1188 (1975) DNA fragments were labeled to an estimated specific activity of 1-2$\times$10$^8$ dpm/µg of DNA. Following nick-translation, an aliquot from each reaction was analyzed by electrophoresis on 4% polyacrylamide gels under denaturing conditions and autoradiographed. Nick translations suitable for subsequent hybridization exhibited a near even distribution of fragment lengths between 100 and 700 nucleotides.

DBM Transfer, Hybridization, and Detection of Sequences in Cellular DNAs

In some instances, hybridization can occur directly on the gel, thereby eliminating the DBM transfer step. As to that step, details for preparing DBM paper and transferring DNA are as given in Bittner et al., Ana. Chem. 102, 459-471 (1980), with the exception that aminobenzyloxymethyl (ABM) paper was made according to Levy et al. Gene 11, 283-290 (1980). For these studies, 20 µg of cellular DNA was digested with four-fold excess Dde I restriction endonuclease (1 hour units) overnight under conditions suggested by the manufacturer (New England Biolabs). Samples were phenol extracted, precipitated with ethanol, and resuspended in TEA buffer before electrophoresis on 5% polyacrylamide TEA gels at 90 V for 18 hrs at room temperature. The DNA was denatured at 4° C. for 20 minutes in 0.2 M NaOH and 0.6 M NaCl, then equilibrated for 1 hour with several changes of transfer buffer (25 mM sodium phosphate buffer, pH 6.5). Electrophoretic transfer to diazobenzyloxymethyl (DBM) paper was conducted as a currect flux of 2 amps for 90 minutes.

Conditions for pretreatment and hybridization to DBM-paper are given by Walh et al. Proc. Natl. Acad. Sci. USA 76, 3683-3687 (1979). However, formamide was omitted, the incubation temperature was increased to 55° C., and the probe was allowed to hybridize for 48 hrs. After hybridization, the DBM paper was washed once in 6XSSC, 0.5% SDS at room temperature, followed by successive washing in 6×SSC, 3×SSC, 1×SSC, and 0.3×SSC. Each of the latter steps was performed twice at 55° C. for 30 minutes and all solutions contained 0.5% SDS. The DBM paper was dried and exposed to Kodak XRP-5 X-ray film using DuPont Lightning-Plus intensifying screens for 2 to 8 days. Experiments involving recombinant DNA were conducted at P2-EK1 containment in accordance with NIH guidelines.

In addition to the radioactive probes to facilitate autoradiographic localization of the hybridization sites, as described above, probes for visualizing DNA fragments can be produced by incorporating protein or biotin coupled nucleotides into a hybridization probe, in accordance with the work of Langer et al. at the Yale University School of Medicine. Once incorporated into the probe, those nucleotides can allow visualization of the $\beta$ globin gene fragments through the use of fluorescent antibodies to the protein or biotin molecules, the antibodies being coated on the filter paper. Such antibodies will bind specifically to DNA fragments to which hybridization has occurred and, in turn, can be visualized by illumination with ultraviolet light.

RESULTS

Rationale of the Analysis

Hb S has been shown to be the result of a single nucleotide base mutation in the $\beta$ globin gene which converts the glutamic acid codon (GAG) at amino acid position 6 to one for valine (GTG). Marotta et al., J. Biol. Chem. 25, 5040-5043 (1977). As shown in Table 1, the A to T transversion within the $\beta$ globin gene sequence affects a restriction endonuclease recognition site for both enzymes Mnl I (GAGG) and Dde I (CTNAG, where N=any base).

TABLE I

A COMPARISON OF THE SICKLE CELL MUTATION SITE IN Hb A AND Hb S

| Type of Hemoglobin | Amino Acid Sequence (Codons 5, 6 and 7) Corresponding Nucleotide Sequence | | |
|---|---|---|---|
| Hb A | pro CCT | glu GAG | glu GAG |
| Hb S | pro CCT | val GTG | glu GAG |

The direct analysis of the present invention was first approached by digestion of genomic $\beta$ globin clone $\beta$ Pst with restriction endonuclease Dde I. This study allowed a mapping of the expected fragments for the normal $\beta$ globin gene. In addition, a probe was isolated which was specific for the 5' end of the genomic $\beta$ globin gene. This probe simplifies the analysis by restricting the studies to DNA fragments complementary to the probe and, therefore, to the 5' region of the $\beta$-like genes.

Restriction Endonuclease Digestion of $\beta$ pst

FIG. 1 shows a restriction map or an illustration of where restriction enzymes cut that part of the $\beta$-globin region complementary to the Alu I (727 bp) probe. The representation of restriction sites within and around the human $\beta$ globin gene was reproduced in part from Lawn et al. Cell 21, 647-652 (1980). For consistency, their method for numbering restriction sites from the intragenic reference point (R) for Bam H1 cleavage has been maintained. The protein encoding regions (filled areas), intervening sequences (open areas), noncoding regions (hatched areas), and the sequenced portion of the 5' intergenic region (wavy line) are indicated. The approximate location of additional restriction sites is so indicated ($\sim$). Fragment lengths generated by Dde I cleavage of normal $\beta$ and the sickle cell $\beta^s$ alleles within the region of probe complementarity are given below in the expanded portion of the restriction map. Numbers represent base pair fragment lengths.

To determine the feasibility of using Dde I successfully, the known $\beta$ globin gene sequence was first analyzed for Dde I cleavage sites within the 5' end of the $\beta$ globin gene up to the Bam H1 site (FIG. 1). This analysis showed Dde I cleavage sites 33 bp, 122 bp, 210 bp, and 411 bp from the Bam H1 reference site, with the 411 bp site being affected by the sickle cell mutation. An analysis of the known DNA sequences within the intergenic region, 103 bp 5' to the $\beta$ globin gene, (where 5' is defined as that region leftward of the reference point and encompassing all DNA base sequences transcribed before reaching the sickle cell mutation site) failed to indicate any Dde I cleavage site. Therefore, digestion of the normal $\beta$ globin gene with Dde I, followed by blot hybridization with 5' specific probe, should reveal two fragments over 100 bp: one fragment of 201 bp representing the DNA restriction fragment 3' from the sickle cell site (where 3' is defined as all DNA base sequences following the sickle cell mutation suite with respect to transcription) and another fragment 170+ bp (103 bp intergenic, 53 bp untranslated and 14 bp translated region) representing the region 5' to the sickle cell mutation site. For the purpose of discussion, these fragments will be referred to as the 3' or 5' fragment.

The identification of the 5' fragment was made by digestion of the 1.8 kb Bam H1 fragment (see Materials and Methods) with Dde I and Dde I+Hae III. A digestion of the 1.8 kb Bam H1 fragment with Dde I produced approximately 460, 285, 210, 201, 175, 170, 105, 88 and 89 bp fragments. The 201, 88 and 89 bp fragments were expected from the gene sequence and were known not to be the 5' fragment. Since the minimum fragment size expected was 170+, the 105 bp Dde I fragment was also eliminated. Base sequence analysis also showed that within the 5' fragment, there is a Hae III site 143 bp from the Dde I site. Therefore, the 5' gene fragment was identified by redigestion with Hae III and the subsequent assay for the fragment which was converted to 143 bp. A double digest (Dde I+Hae III) showed that the 460, 210, and 170 bp fragments were not cut by Hae III, and that the 285 bp fragment was converted to a 265 bp fragment. Therefore, the 175 bp fragment that was cut by Hae III to 143 bp, must include the 5' end of the $\beta$ globin gene. Consequently, Dde I analysis of the normal $\beta$ globin gene would be expected to show two fragments, 201 and 175 bp, complementary to the specific probe. Digestion of homozygous Hb S DNA should show a single fragment of 376 bp complementary to the specific β globin probe.

Characterization of the probe

A fragment approximately 855 bp, specific to the 5' region of the β-globin gene was expected from the restriction map presented according to Lawn et al. Cell 21, 647–652 (1980). When subsequent redigestions with Hae III were performed, only one fragment gave the predicted pattern (FIG. 1). However, a slight discrepancy in the length of one Hae III fragment was observed which indicates the existence of an additional Alu I site in the 5' intergenic region. This may be due to the creation of new Alu I site during the construction of this clone. As a consequence, however, the actual length for the Alu I probe is 737 bp, rather than the anticipated 855 bp. Furthermore, blot hybridizations using $^{32}$P-Alu I (737 bp) hybridized to Hae III and Dde I digests of cloned β-globin gene have also given the expected banding patterns.

Blot Hybridization Analysis of Hb S Gene

Figure 2:
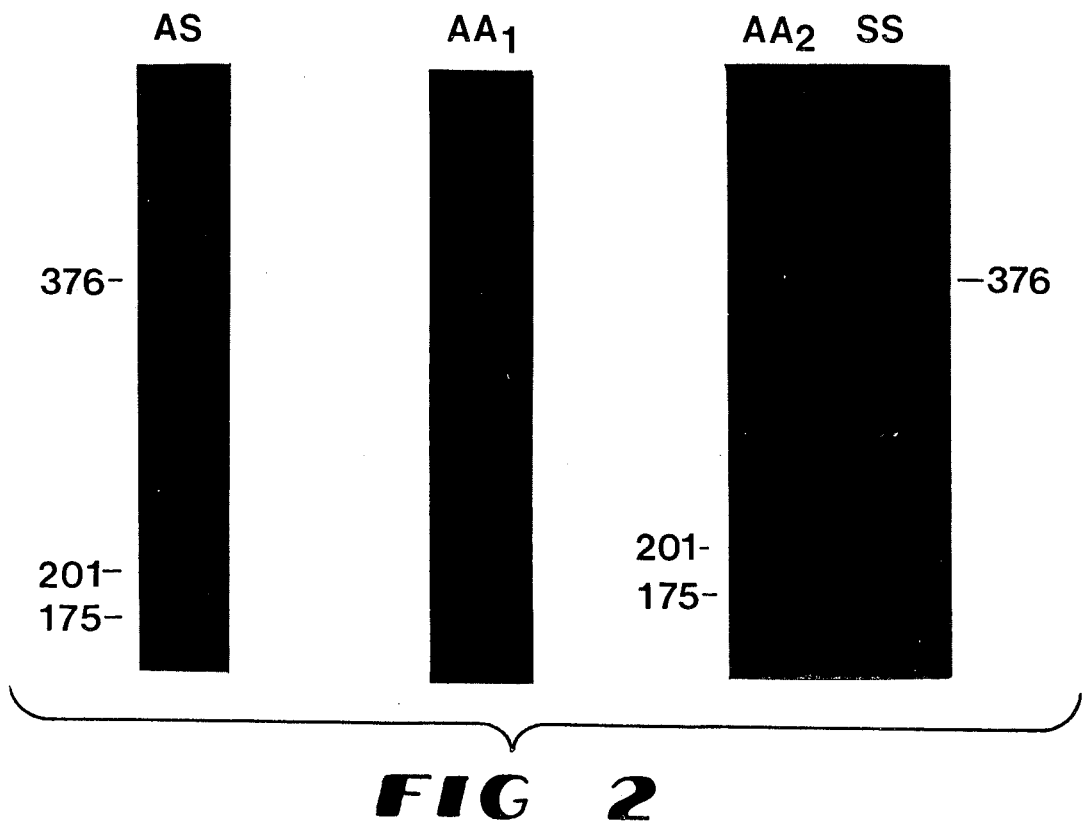
FIG. 2 is a photograph of autoradiograms of sickle cell (SS), sickle cell trait (AS), and two control individuals (AA, and AA$_2$) prepared by the present invention.

Following the preliminary studies, blot hybridization analyses were performed on Dde I digested lymphocyte and amniotic fluid cell DNAs. Lymphocyte DNAs was obtained from normal, sickle cell and sickle cell trait individuals, whereas amniotic fluid cell DNA was obtained by amniocentesis on a woman carrying a fetus at risk for sickle cell anemia. Autoradiograms of DNA samples isolated from peripheral blood lymphocytes are presented in FIG. 2. As can be seen, DNA from control individuals (AA) show both the approximate 175 and 201 bp bands whereas sickle cell DNA (SS) shows the 376 bp band. DNA from sickle cell trait individual (AS) shows the expected combination of 175, 201 and 376 bp bands. The presence of larger additional bands may be the result of a slight contamination of the probe with other DNA fragments. Such contamination is most probably due to the difficulty in isolating the 5' specific probe free from adjacent DNA fragments. Repeated experiments with DNA obtained from different individuals have shown these larger bands to be consistent for AA and SS individuals. These bands are also present in blot hybridizations from Dde I digestions of the β Pst (4.4) plasmid (data not shown). Purification of the 5' specific probe by recombinant DNA techniques (see the following discussion) should eliminate these bands.

Discussion

The above analysis of Dde I digested normal, sickle cell and sickle cell trait DNAs are consistent with expected results. A potential complication in this analysis would result from cross hybridization of the probe with other β-like genes. It has been shown that under stringent conditions, cross-hybridization of β globin genes does not occur. However, due to the close similarity of nucleotide sequence of the δ and β globin DNA, cross-hybridization of the probe with the δ globin gene is detectable even under stringent conditions. A survey of the known globin sequence shows that the 5' δ globin gene fragment would not be 175 bp, but a minimum of 189+ bps. Even though this fragment has not been identified, it does not seem to interfere with the analysis, and should be present in both normal and sickle cell DNA. The known δ globin gene sequence shows also a 199 bp fragment similar to that of the 3' β globin gene fragment. Therefore, the 201 bp band in the analysis probably represents a contribution of restriction fragments from both the δ and β globin gene in the normal DNA, but only the δ globin gene in sickle cell DNA. Since the 201 bp band could only represent the δ globin gene in sickle cell DNA, it would be expected to bind only ½ as much radioactivity in those individuals, compared to normal individuals.

The data presented herein is from analyses which were performed on DNAs isolated from three unrelated sickle cell individuals and two unrelated control individuals. In all cases, the 376 bp band has been present in association with the sickle cell allele. However, in comparing autoradiograms from the same individual and autoradiograms from different individuals, the 201 bp fragment in sickle cell DNA is often not present, or when present, it is very faint. This probably reflects the 12–16% divergence of the δ globin and the β globin gene nucleotide sequence in that region of the DNA complementary to the probe. Since the 201 bp fragment is sometimes present in sickle cell DNA, then the essence for diagnosis of sickle cell anemia is the absence of the 175 bp fragment and the appearance of the 376 bp fragment. Diagnosis of the sickle cell trait is based on the presence of the 175 and 376 bp fragments.

Fetuses heterozygous for Hb S and other hemoglobin disorders, such as Hb C or nondeletion type β-thalassemia, would give blot hybridization patterns identical to sickle cell trait individuals. Naturally, these could be excluded by family studies. Moreover, these disorders are usually less severe than sickle cell anemia.

A feasible approach for detection of sickle cell anemia has been presented. This analysis was conducted on DNA isolated from peripheral blood lymphocytes and DNA isolated by amniocentesis on a woman carrying a fetus at risk for sickle cell anemia. The analysis on the lymphocyte DNA and the amniotic fluid cell DNA accurately portrayed the person's genotype as showing the predicted pattern for the sickle cell allele. Therefore, this invention is applicable to the prenatal or postnatal diagnosis of sickle cell anemia.

Applicants have observed in blot hybridization experiments with humna genomic hemoglobin genes that the use of recombinant DNA molecules, as opposed to isolated restriction fragments, increases the sensitivity of the procedures. This is probably the result of enhanced specific activity and the formation of more extensive hybridization networks. Experiments have been performed in order to insert the 5' specific probe into recombinant DNA molecules. The use of this cloned probe is expected to increase the sensitivity of this method. Also, this resulted in a purification of the 5' specific probe, which eliminated the occurence of additional high molecular weight bands.

In conclusion, additional studies are necessary to determine the degree to which polymorphism in the natural population will interfere with the proposed method. The occurence of polymorphisms that create or eliminate Dde I recognition sites could change the expected blot hybridization pattern. However, since a probe of only 737 bp is being used to assay fragments of 175 and 201 bp, the occurence of a specific polymorphism is expected to be minimal. To date, over 30 individuals have been analyzed by this method and no such polymorphisms have been identified.

What we claim is:

1. A method for the direct analysis of sickle cell anemia in the human β gene, comprising the steps of:

(a) obtaining an effective amount of amniotic fluid cells from a human;
(b) isolating DNA from said cells;
(c) digesting said DNA with restriction enzyme Dde I to form DNA fragments;
(d) separating said DNA fragments according to their respective molecular weights to form a pattern for said fragments on filter paper; and
(e) detecting the absence of an approximate 175 base pair fragment and the presence of an approximate 376 base pair fragment on said pattern, thereby indicating the sickle cell genotype.

2. A method as claimed in claim 1 wherein said separating step includes gel electrophoresis of said DNA fragments.

3. A method as claimed in claim 2 wherein said gels are polyacrylamide gels.

4. A method as claimed in claim 2 further including the step of electrophoretically transferring said DNA fragments to DBM filter paper.

5. A method as claimed in claim 1 wherein said separating step includes isolating said fragments by the use of reversed phase chromatography.

6. A method as claimed in claim 1 wherein said separating step includes directing said fragments through a high pressure reversed phase chromatographic column (RPC-5) to obtain separated fragments and transferring said separated fragments to said filter paper.

7. A method as claimed in claim 1 wherein said detecting step includes hybridizing said separated fragments with a DNA probe.

8. A method as claimed in claim 7 wherein said probe comprises recombinant human DNA having the $\beta$ globin genomic sequence included therein, said sequence labeled with a radioactive nucleotide.

9. A method as claimed in claim 7 wherein said probe comprises recombinant human DNA having the $\delta$ globin genomic sequence included therein, said sequence labeled with a protein-coupled nucleotide.

10. A method as claimed in claim 7 wherein said probe comprises recombinant human DNA having the $\beta$ globin genomic sequence included therein, said sequence labeled with a biotin coupled nucleotide.

11. A method as claimed in claim 8 and further including the step of blot hybridizing said probe with said fragments on said filter paper.

12. A method as claimed in claim 11 including the step of preparing an autoradiogram of the hybridized filter paper.

13. A method as claimed in either claim 9 or claim 10 and further including the step of blot hybridizing said probe with said fragments on said filter paper.

14. A method as claimed in claim 13 and further including the step of coating said filter paper with fluorescent antibodies and illuminating with ultraviolet light.

15. A method for the direct analysis of sickle cell anemia in genomic DNA, comprising the steps of:

(a) digesting said DNA with restriction endonuclease Dde I to generate fragments;
(b) resolving said fragments according to their respective molecular weights;
(c) transferring said fragments to filter paper; and
(d) visualizing said fragments on said filter paper to detect an approximate 376 base pair fragment and the absence of an approximate 175 base pair fragment, thereby determining sickle cell anemia.

16. A method as claimed in claim 15 wherein the steps prior to said digesting step include obtaining an effective amount of amniotic fluid cells from a human and isolating said DNA from said fluid cells.

17. A method as claimed in claim 15 wherein said resolving step includes separating said fragments on polyacrylamide gels.

18. A method as claimed in claim 15 wherein said resolving step includes the step of directing said fragments through a high pressure reversed phase chromatographic column.

19. A method as claimed in claim 15 wherein said visualizing step comprises hybridizing said fragments on said filter paper with a DNA probe.

20. A method as claimed in claim 19 wherein said probe comprises recombinant human DNA having included therein a sequence comprising the 5' end of the $\beta$ globin gene.

21. A method as claimed in claim 20 wherein said sequence includes a radioactive nucleotide.

22. A method as claimed in claim 21 and further including the step of preparing an autoradiogram of the hybridized filter paper.

23. A method as claimed in claim 20 wherein said sequence includes a protein-coupled nucleotide.

24. A method as claimed in claim 20 wherein said sequence includes a biotin-coupled nucleotide.

25. A method as claimed in either claim 23 or claim 24 and further including the steps of binding a fluorescent antibody to said nucleotide and illuminating said filter paper with ultraviolet light.

26. A method for the direct analysis of sickle cell anemia in genomic DNA, comprising the steps of:

(a) digesting said DNA with a restriction enzyme which recognizes the nucleotide base sequence CTNAG wherein N is any base to produce fragments;
(b) separating said fragments according to their respective molecular weights;
(c) hybridizing said fragments with a DNA probe; and
(d) visualizing said pattern to determine if the recognition sequence of said restriction enzyme is created or eliminated by the sickle cell allele, the elimination of said sequence indicating the presence of sickle cell genotype.

27. A method as claimed in claim 26 wherein said restriction enzyme is Dde I.

* * * * *